US010864125B2

United States Patent
Louwrens (10) Patent No.: US 10,864,125 B2
(45) Date of Patent: *Dec. 15, 2020

(54) GOWN SYSTEM

(71) Applicant: Neil Andrew Louwrens, Redding, CA (US)

(72) Inventor: Neil Andrew Louwrens, Redding, CA (US)

(73) Assignee: GownUP Inc., Redding, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/842,084

(22) Filed: Apr. 7, 2020

(65) Prior Publication Data

US 2020/0237584 A1    Jul. 30, 2020

Related U.S. Application Data

(60) Continuation of application No. 16/037,230, filed on Jul. 17, 2018, now Pat. No. 10,653,572, which is a division of application No. 15/862,061, filed on Jan. 4, 2018, now Pat. No. 10,022,282, which is a division of application No. 15/467,242, filed on Mar. 23, 2017, now Pat. No. 9,861,537.

(60) Provisional application No. 62/316,983, filed on Apr. 1, 2016.

(51) Int. Cl.
| | |
|---|---|
| *B65D 85/18* | (2006.01) |
| *A61F 15/00* | (2006.01) |
| *A41D 13/12* | (2006.01) |
| *B65D 83/08* | (2006.01) |
| *B65D 25/22* | (2006.01) |

(52) U.S. Cl.
CPC ............ *A61F 15/001* (2013.01); *A41D 13/12* (2013.01); *A41D 13/1209* (2013.01); *B65D 25/22* (2013.01); *B65D 83/0805* (2013.01); *B65D 85/18* (2013.01)

(58) Field of Classification Search
None
See application file for complete search history.

(56) References Cited

U.S. PATENT DOCUMENTS

| | | | |
|---|---|---|---|
| 5,622,281 | A | 4/1997 | Annand |
| 9,861,537 | B2 * | 1/2018 | Louwrens ............. A61F 15/001 |
| 10,022,282 | B2 * | 7/2018 | Louwrens .......... B65D 83/0805 |
| 10,653,572 | B2 * | 5/2020 | Louwrens ............. A61F 15/001 |
| 2005/0199690 | A1 | 9/2005 | Peterson |
| 2013/0105511 | A1 | 5/2013 | Graneto, III |
| 2013/0318682 | A1 | 12/2013 | Graneto, III |

* cited by examiner

*Primary Examiner* — Gene O Crawford
*Assistant Examiner* — Ayodeji T Ojofeitimi
(74) *Attorney, Agent, or Firm* — Entralta P.C.; Justin G. Sanders; Peter D. Weinstein (57) ABSTRACT

A gown dispenser system has a plurality of gowns, each having a back region, the gowns folded and stacked back region facing up, such that, pulling on the back region of a gown on top of the stack removes that gown from the stack and exposes the back region of the next gown in the stack, an enclosure containing the stack of gowns, the enclosure having an opening exposing the back region of the gown at the top of the stack, enabling a user to grasp the exposed back region and pull the topmost gown from the enclosure, exposing the next gown in the stack. Gowns are drawn from the enclosure one-at-a-time, at need.

20 Claims, 6 Drawing Sheets

GOWN SYSTEM

RELATED APPLICATIONS

This is a continuation application and so claims the benefit pursuant to 35 U.S.C. § 120 of a prior filed and U.S. non-provisional patent application Ser. No. 16/037,230, filed on Jul. 17, 2018, which itself is a divisional application of U.S. non-provisional patent application Ser. No. 15/862,061, filed on Jan. 4, 2018 (now U.S. Pat. No. 10,022,282, which issued on Jul. 17, 2018), which is a divisional of U.S. non-provisional patent application Ser. No. 15/467,242, filed on Mar. 23, 2017 (now U.S. Pat. No. 9,861,537, which issued on Jan. 9, 2018), which claims priority pursuant to 35 U.S.C. § 119(e) to and is entitled to the filing date of U.S. provisional patent application Ser. No. 62/316,983, filed on Apr. 1, 2016. The contents of the aforementioned applications are incorporated herein by reference.

BACKGROUND

The invention is in the technical area of dispensing items, such as garments, and has particular application in sanitation in medical practice, and pertains in one embodiment more particularly to providing hospital gowns to medical staff.

Applicant hereby incorporates herein by reference any and all patents and published patent applications cited or referred to in this application.

By way of background, in many technical arts, disposable items are provided for temporary use. Many examples may be listed, such as gloves in both medical and food arts, aprons in food arts, and sanitary gowns in medical environments. Medical practice is a particular, but not a limiting focus, for applications of the instant invention, and is used exemplary below to describe specific examples as embodiments of the present invention.

It is often necessary in medical practice for a physician, nurse or other medical practitioner to quickly don a hospital gown before entering a sanitary area. The present invention provides a quick and practical solution to this need. Aspects of the present invention fulfill these needs and provide further related advantages as described in the following summary.

It should be noted that the above background description includes information that may be useful in understanding aspects of the present invention. It is not an admission that any of the information provided herein is prior art or relevant to the presently claimed invention, or that any publication specifically or implicitly referenced is prior art.

SUMMARY

Aspects of the present invention teach certain benefits in construction and use which give rise to the exemplary advantages described below.

In one exemplary embodiment of the invention, a gown dispenser system is provided, comprising a plurality of gowns, each having a back region, the gowns folded and stacked back region facing up, such that, pulling on the back region of a gown on top of the stack removes that gown from the stack and exposes the back region of the next gown in the stack, an enclosure containing the stack of gowns, the enclosure having an opening in one surface exposing the back region of the gown at the top of the stack, enabling a user to grasp the exposed back region and pull the topmost gown from the enclosure, exposing the next gown in the stack. Gowns are drawn from the enclosure one-at-a-time, at need.

In one embodiment, a pull tab is attached to the back region of each gown in the stack, providing an appendage to be grasped to pull a gown from the enclosure. Also in one embodiment of the system, the enclosure is implemented in paperboard, with a portion of the paperboard on the one surface of the enclosure perforated in a shape to provide the opening, with the paperboard within the perforated region removed. Also in one embodiment, the interface mechanism comprises one or more brackets attached to a side of the container opposite the side perforated for the opening, the brackets configured to enable hanging the container from a top edge of a door. In one embodiment, the front portion has tie extensions extending horizontally from opposite edges of the front portion, at a height for tying the front portion of the gown around the body of a user. And in one embodiment the gowns are folded by folding the left and right sleeves to the front along edges of the front portion, and a lower part of the front portion upward to the front along a substantially horizontal line, leaving the tab free at the back of the upper portion of the folded gown.

In another aspect of the invention, a method for providing a gown to a user from a gown-dispensing system is provided, comprising folding a plurality of gowns having a back region of each gown in a stack with the back region facing up, and placing the gowns in an enclosure having a front and a back surface, the back surface having an opening exposing the back region of the top-most gown on the stack, grasping the back region by a user and pulling a topmost gown out through the opening in the back surface, leaving a next gown in the stack having the pull tab exposed through the opening, and donning the gown. In one embodiment of the method a pull tab is attached to the back region of each gown in the stack, and the pull tab is grasped to pull a gown from the enclosure.

In one embodiment of the method, each gown in the stack has an upper portion having a front region and the back region, a left and a right sleeve, each of a length to cover an arm of a person, and an upper head opening, the back region extending to a lower extremity of the left and right sleeves, a front apron portion, having a width from the left to the right sleeve, extending downward from the upper portion for a height to cover a major portion of a person's body below the extension of the left and right sleeves, and the gowns are folded by folding the left and right sleeves to the front along edges of the front portion, and folding a lower part of the front portion upward to the front along a substantially horizontal line, leaving the back region free at the back of the upper portion of the folded gown, and the method further comprises the user pulling the upper portion over the user's head and placing the head through the upper head opening, and the user stepping back away from the enclosure, pulling the balance of the gown from the enclosure.

Other features and advantages of aspects of the present invention will become apparent from the following more detailed description, taken in conjunction with the accompanying drawings, which illustrate, by way of example, the principles of aspects of the invention.

BRIEF DESCRIPTION OF THE DRAWINGS

The accompanying drawings illustrate aspects of the present invention. In such drawings.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

DETAILED DESCRIPTION

Figure 1A:
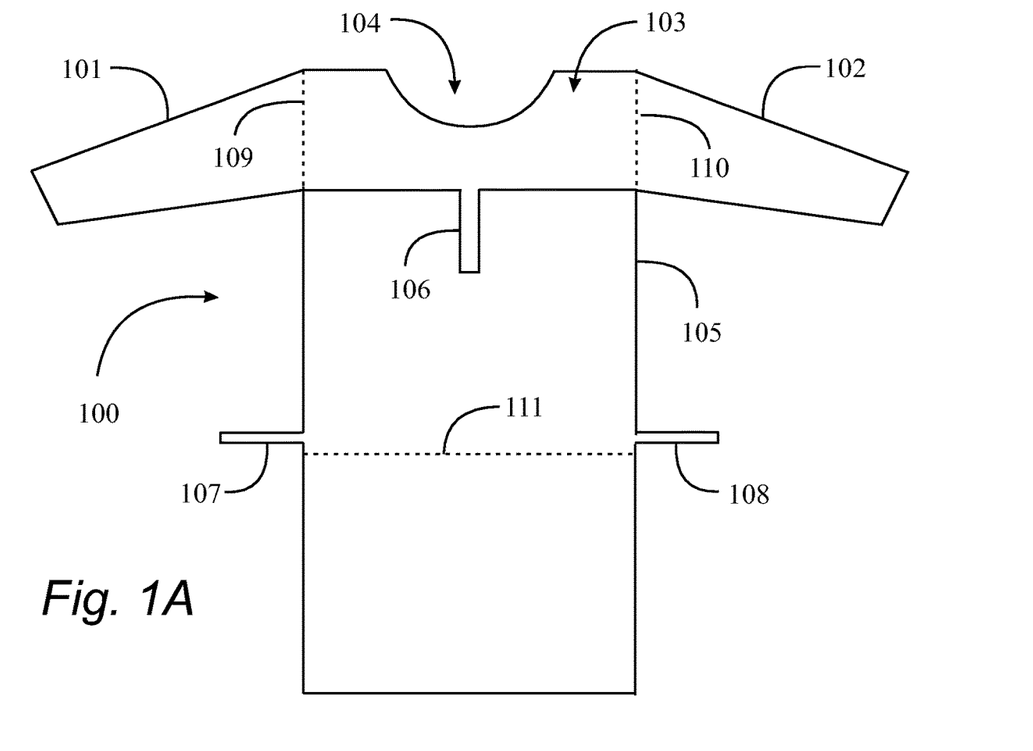
FIG. 1A is an illustration of a hospital gown in an embodiment of the invention, in accordance with at least one embodiment.

FIG. 1A is an illustration of a hospital gown 100 in an embodiment of the invention. In this view, the gown is fully deployed (not folded) and is viewed from the back of the gown. Gown 100 has a contiguous upper portion 103 that applies over a user's shoulders, with an opening 104 for the user's head, and has a left arm portion 101 and a right arm portion 102. It will be apparent to the skilled person that, as shown in FIG. 1B, upper portion 103 and arm portions 101 and 102 have two layers, to fit over the shoulders, front and back, and to cover the arms when the gown is worn.

Upper portion 103 has an extension 106, extending from the layer of portion 103 to the back of the gown, which serves as a pull-tab in deploying the gown for use, as is described in enabling detail below. A single layer lower portion 105 extends below the upper portion to a lowermost extremity, and is contiguous with the front of upper portion 103. If one were to grasp tab 106 and pull in the direction out of the figure, upper portion 103 would open, presenting opening 104 for the user's head, and the gown could be donned by pulling upper portion 103 over the head, and down so the user's head passes through opening 104, which would leave lower portion 105 to the user's front.

Gown 100 further comprises two extensions as tie-tabs 107 and 108, laterally to each side in FIG. 1A. These tie-tabs act as ties once the user dons the gown, to tie lower portion 105 around the user's torso. Further, FIG. 1A illustrates fold lines 109, 110, and 111, which are lines along which the gown may be folded to be placed in a dispenser in an embodiment of the invention described in enabling detail below.

Figure 1B:
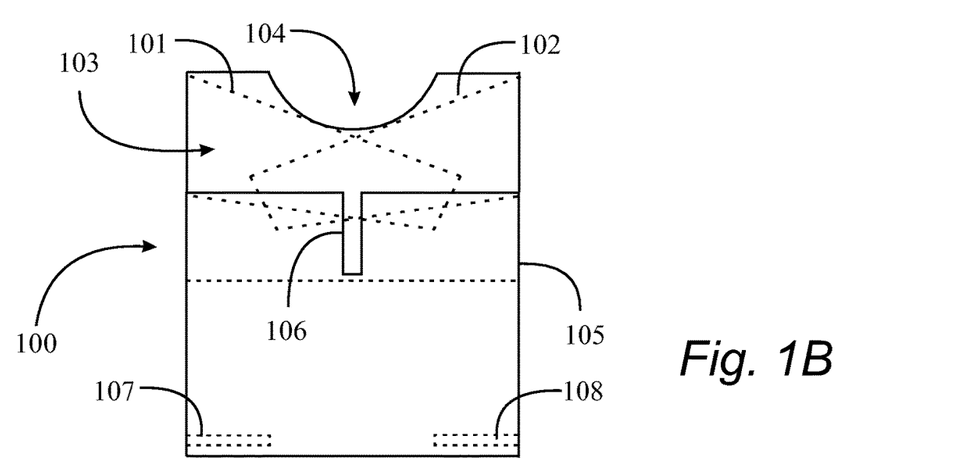
FIG. 1B is an illustration of the gown of FIG. 1A folded, in accordance with at least one embodiment.

FIG. 1B is an illustration of gown 100 of FIG. 1A folded along fold lines 109, 110 and 111. Each of tie-tabs 107 and 108 has a fold line at the edge of lower portion 105, but these fold lines are not shown in FIG. 1A. Sleeves 101 and 102 are folded along fold lines 109 and 110 respectively, to the front (into the plane of the figure), to lie against the front of the gown as shown in FIG. 1B. Tie-abs 107 and 108 are also folded to the front to lie against the front of the gown. Lastly the portion of the gown below fold line 111 is also folded up to the front along fold line 111, to lie against the front of the gown. After these operations, the folded gown is as seen in FIG. 1B.

In alternative embodiments, the tie-tabs might be in different positions on a gown, and in one embodiment two tie-tabs may be joined to the gown on the same side. The position, length, and use of the tie-tabs in ties on a gown after the gown is donned is related to specific practice in particular circumstances, and the tie-tabs are not limiting in their position, length and the like.

Figure 2:
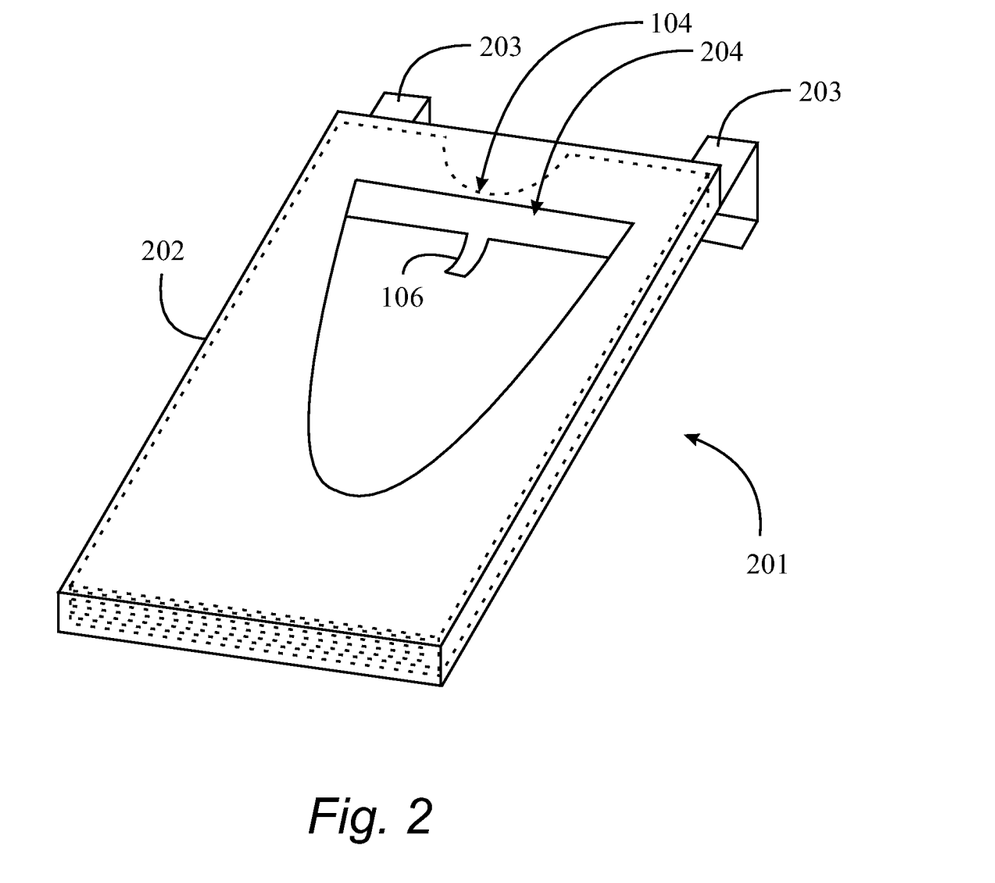
FIG. 2 is an illustration of a dispenser for providing folded gowns one-at-a-time to users, in accordance with at least one embodiment.

FIG. 2 is an illustration of a dispenser 201 for providing folded gowns one-at-a-time to users. Dispenser 201 comprises a container 202 with one or more interfaces 203 for suspending the container from a vertical surface, such as a wall or a doorway. A plurality of folded gowns, folded according to FIG. 1B in one embodiment, is enclosed in a stack in container 202. Container 202 has an opening 204 on one major surface for allowing gowns to be presented to users, and for gowns to be withdrawn and donned by users.

It is emphasized that mounting on a vertical surface, such as a wall or a doorway, is a convenience and an option, not a limitation in the invention. In some cases, a dispenser may be mounted to a chair back, simply placed on a table or other supporting surface, or provided in many other ways. The important issue is that a user must be able to access a gown from the dispenser and don the gown in a sanitary fashion.

A stack of folded gowns within container 202 is positioned such that, when opening 204 is provided, in a manner described below, tab 106 of a topmost gown in the stack is presented, and is physically accessible to a user, such that the user may grasp the tab and pull, to at least partially dispense the connected gown from the container. The neck opening 104 of the topmost folded gown in the stack of gowns in container 202 is seen in dotted outline in FIG. 2.

In some embodiments of the invention it is important to certain persons to know when there is a limited number of gowns left in the dispenser. For this purpose, in one embodiment, the last few gowns in a dispenser container, for example the last five, may have a specific indicator, like a red dot, or other visible indicia, so users know there are only a limited supply left. In one embodiment radio-frequency identification (RFID) may be used to track the number of gowns in a container, and to alert when the number falls to a critical number. In this method, electronically-discoverable tags are attached, one to each gown. RFID uses electromagnetic fields to automatically identify and track the tags attached to gowns. The tags contain electronically stored information. Passive tags collect energy from a nearby RFID reader's interrogating radio waves. Another use for such mechanisms is for monitoring compliance with gown use—in which case detection of the gown 100 may be performed at the container 202 or alternatively within a doorway for when the user passes therethrough. In such embodiments, the RFID reader may be a part of the container, or placed near the container, and may have a transmitter to send an alert to an external device, which may be as simple as a cell phone of a person responsible for being sure gowns are available and/or are being worn.

Container 202 may be constructed of a variety of materials, such as plastic, metal, or other materials now known or later developed; but in one embodiment a preferred material is paperboard of a thickness and strength to maintain its shape when handled, and when hung on a door or a wall. In various embodiments opening 204 may be shaped differently than shown in FIG. 2, and some shapes may facilitate feeding of individual gowns from the container. In addition, interfaces 203 may be provided in a variety of ways.

In one embodiment, wherein container 202 is constructed of paperboard, opening 204 is closed, but the outline seen in FIG. 2 is perforated in the material of the container, such that a user may remove the covering over the opening, presenting gowns accessible through the opening.

In an alternative embodiment, a separate outside container or support structure may be provided, made of more rigid material, like plastic et or metal, and may be structured for a paperboard or other container of gowns to be placed in the outside container.

In the circumstance of a paperboard container, the container itself may be throwaway, so when the last gown is withdrawn, the container is just discarded, and a new container full of gowns is placed for service. In another embodiment, gowns may be replaceable in pre-stacked groups, perhaps in a sanitary covering that may be removed. In this circumstance container 202 may be of more sturdy construction, and may have a side opening that may be opened to allow a new stack of gowns to be inserted for use. In this circumstance the container may be designed to be cleanable, to be kept in sanitary condition. In some cases, the opening for a new stack of gowns may be in the top or bottom edge, or anywhere else, such that the stack of gowns may be inserted.

Figure 3:
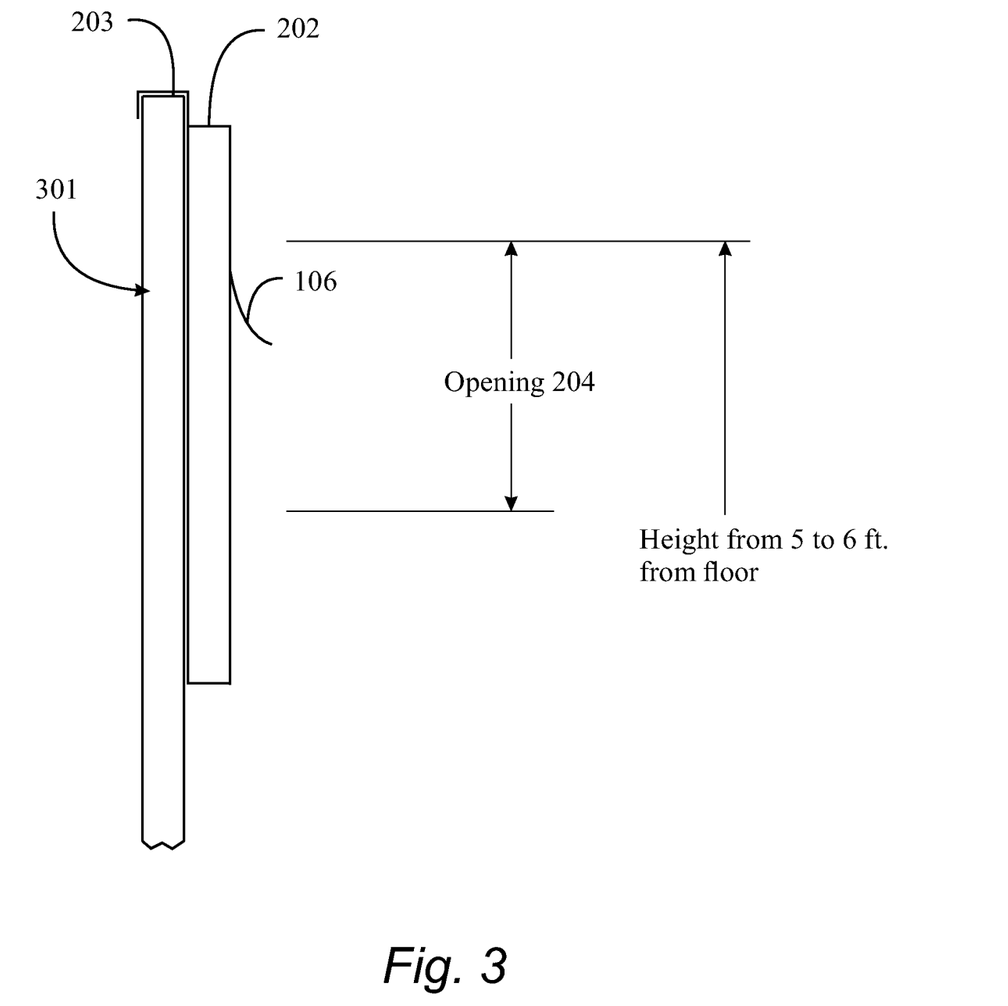
FIG. 3 is an illustration of the dispenser of FIG. 2 hung on a door, in accordance with at least one embodiment.

FIG. 3 illustrates container 202 suspended on a door 301 by interfaces 203 engaging the top of the door. Opening 204 faces outward, away from door 301, positioned at a height between 5 and 6 feet in one embodiment. Opening 204 height is shown, and tab 106 may be seen extending out from opening 204, such that a user may easily grab and pull on the tab.

Figure 4A:
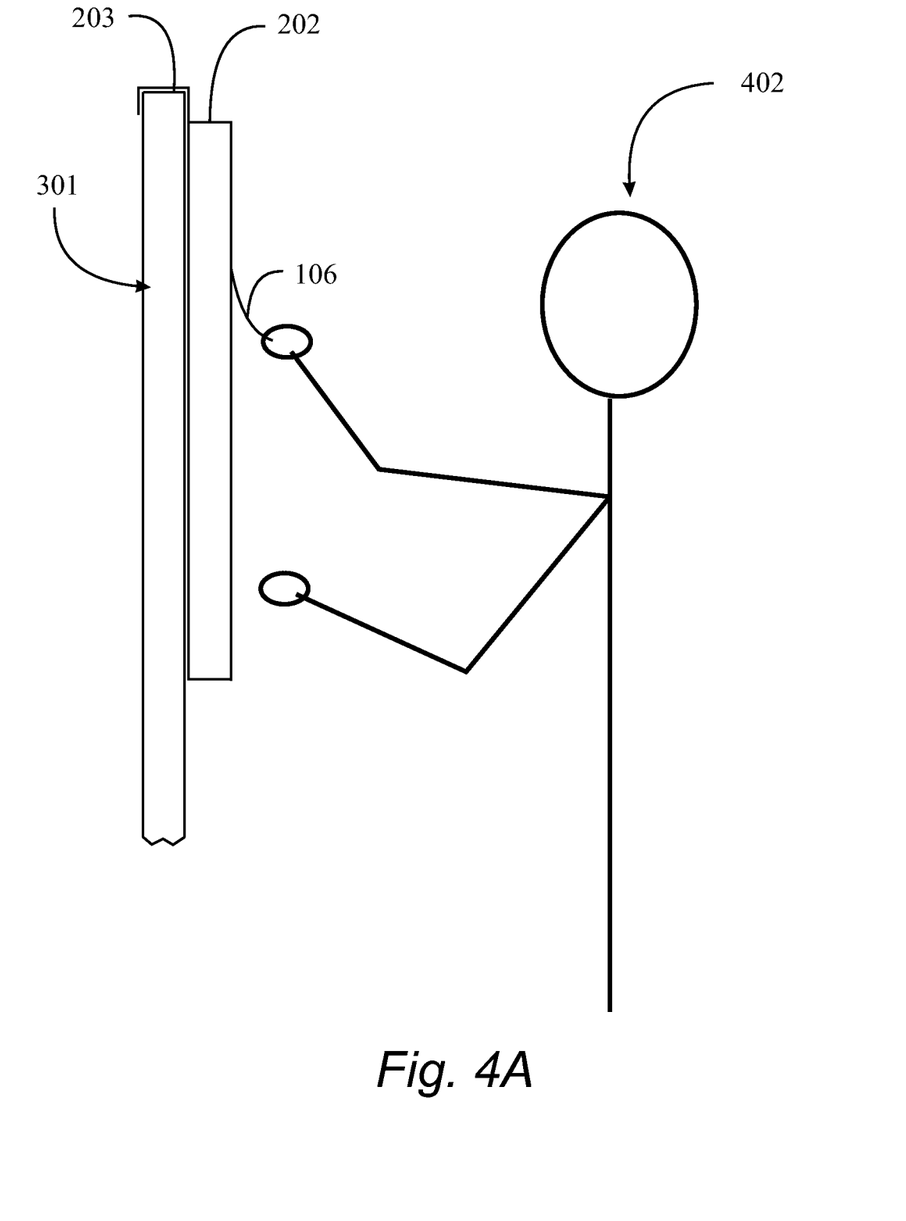
FIG. 4A is an illustration showing a person about to draw a gown from the dispenser of FIG. 3, in accordance with at least one embodiment.

FIG. 4A illustrates a user 402, who may be a doctor or nurse, for example, reaching for and grasping tab 106 of a topmost gown in container 202 hung on door 301. In this example, it may be assumed that the door is entry to a hospital room or an operating theatre where a gown may be mandatory; though in further embodiments, the container 202 may be hung anywhere else that gowns may be needed, such as a wall, ambulance door, or in any non-healthcare environment also in need of same gowns, etc.

Figure 4B:
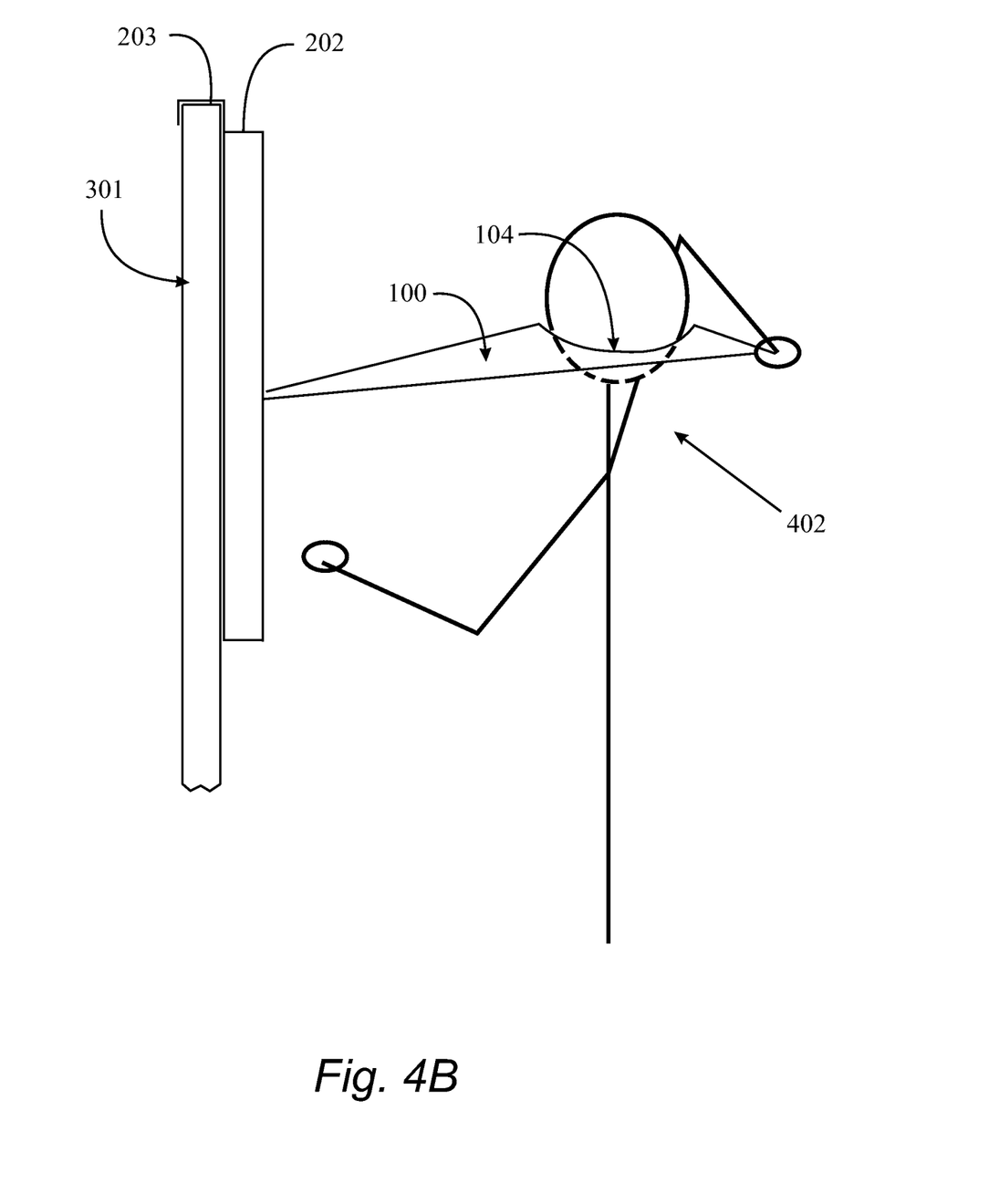
FIG. 4B is an illustration illustrating a second step in withdrawing a gown from the dispenser, in accordance with at least one embodiment.

FIG. 4B illustrates user 402, having pulled a gown 100 partly from container 202, and having pulled the gown over his/her head, with the head now projected upward through opening 104 at the top of the upper portion of the gown. The folding of gown 100 and placement into container 202 presents the tab 106 at a convenient height for the user to grasp the tab and pull the gown, and the placement of the gown with back facing outward allows the step of pulling the gown over the user's head.

Figure 4C:
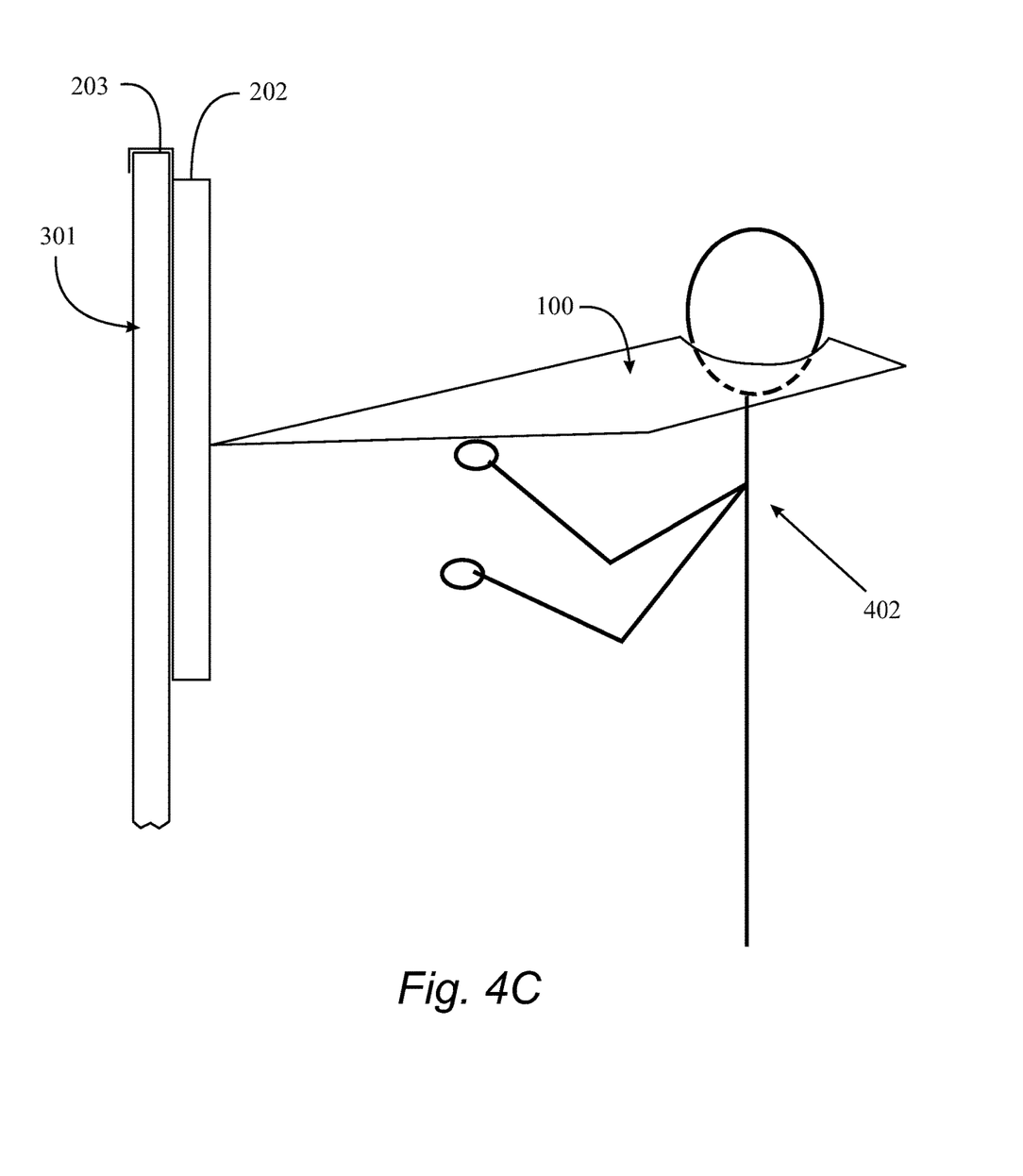
FIG. 4C is an illustration of a third step in withdrawing a gown from the dispenser, in accordance with at least one embodiment.

FIG. 4C illustrates a third step, wherein the user, with his or her head through opening 104 of the gown, releases the gown with the hand that grasped the tab, and simply steps backward one or two steps, away from the dispenser, which action causes gown 100 to fully draw out of the dispenser. At this point the front of the gown may fall down in front of the user, and the user may easily put his/her arms into the sleeves of the gown, and then tie the gown around the torso. This final step is not shown, but will be fully apparent to the skilled person.

In one embodiment, the dispenser, including container 102, and gowns in or to be placed into the container, are provided fully sterilized, and protected in sterile form, into a sterile environment, such as an operating theatre. In yet another embodiment gowns in this invention may have a tie tab from one gown physically connected to a portion of a next gown in a stack. This version is useful in a procedure for donning gowns, that may be used in a sterile environment to prevent contamination in the process of donning a gown.

It is emphasized as well that gowns, to be compatible with aspects of this invention, need not be exactly the form and folding shown in FIGS. 1A and 1B, but may be made in some cases considerably differently. In one embodiment gowns provided for use in aspects of this invention have thumb holes in the ends of the sleeves, in a position that a wearer can pass his or her thumb through this opening, beforehand coverings are applied, which prevents the arms of the gown from riding up when the wearer is busy in performing tasks.

It will also be apparent to the skilled person that the embodiment described above with regard to FIGS. 1-4C is an example, and not limiting. The examples provided above are just that, examples, exemplary of specific implementations of the invention, and not limiting. The invention has application far beyond provision of gowns in a hospital setting. Further, the gowns may be plastic or fabric of many sorts, and may be designed and implemented in a variety of ways, and also folded in a variety of ways. There are many alterations to the gown, the container, the openings, and the placement of the dispenser on a vertical surface that will fall within the scope of the invention. In some embodiments, the interfaces to the vertical surface may vary, both in form and number.

In some embodiments, the opening in the container to present a gown for withdrawal may be different in shape and size. There are many options within the scope of the invention.

In closing, regarding the exemplary embodiments of the present invention as shown and described herein, it will be appreciated that a gown dispenser system is disclosed. Because the principles of the invention may be practiced in a number of configurations beyond those shown and described, it is to be understood that the invention is not in any way limited by the exemplary embodiments, but is generally directed to a gown dispenser system and is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention.

Certain embodiments of the present invention are described herein, including the best mode known to the inventor(s) for carrying out the invention. Of course, variations on these described embodiments will become apparent to those of ordinary skill in the art upon reading the foregoing description. The inventor(s) expect skilled artisans to employ such variations as appropriate, and the inventor(s) intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein. Similarly, as used herein, unless indicated to the contrary, the term "substantially" is a term of degree intended to indicate an approximation of the characteristic, item, quantity, parameter, property, or term so qualified, encompassing a range that can be understood and construed by those of ordinary skill in the art.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.—for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (along with equivalent open-ended transitional phrases thereof such as "including," "containing" and "having") encompasses all the expressly recited elements, limitations, steps and/or features alone or in combination with un-recited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amendment for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim, whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (along with equivalent open-ended transitional phrases thereof) includes within its meaning, as a limiting case, claimed subject matter specified by the closed-ended transitional phrases "consisting of" or "consisting essentially of." As such, embodiments described herein or so claimed with the phrase "comprising" are expressly or inherently unambiguously described, enabled and supported herein for the phrases "consisting essentially of" and "consisting of."

Any claims intended to be treated under 35 U.S.C. § 112(f) will begin with the words "means for," but use of the term "for" in any other context is not intended to invoke treatment under 35 U.S.C. § 112(f). Accordingly, Applicant reserves the right to pursue additional claims after filing this application, in either this application or in a continuing application.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicant and does not constitute any admission as to the correctness of the dates or contents of these documents.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A gown dispenser system, comprising:
a plurality of gowns, each gown comprising:
an upper portion having a front region and an opposing back region;
opposing left and right arm openings positioned in the upper portion; and
a head opening positioned in the upper portion;
the plurality of gowns folded and stacked with the back region of each gown facing up, such that, grasping and pulling on the back region of a gown on top of the stack removes that gown from the stack and exposes the back region of the next gown in the stack; and
an enclosure containing the stack of gowns with the back regions facing up, the enclosure having an opening in one surface exposing at least a portion of the back region of the gown at the top of the stack, enabling a user to grasp the exposed back region, and to pull the topmost gown from the enclosure, exposing the next gown in the stack.

2. The gown dispenser system of claim 1, further comprising an interface mechanism attached to the enclosure, enabling the enclosure to be suspended on a substantially vertical surface, with the opening facing outward from the substantially vertical surface.

3. The gown dispenser system of claim 1, wherein the enclosure is implemented in paperboard, with a portion of the paperboard on the one surface of the enclosure perforated in a shape to provide the opening, with the paperboard within the perforated region removable.

4. The gown dispenser system of claim 1, wherein each gown further comprises a front apron portion integral with and extending downwardly from the front region.

5. The gown dispenser system of claim 4, wherein the back region has a length that is shorter than the front apron portion.

6. The gown dispenser system of claim 4, wherein the front apron portion has a length sufficient for covering a major portion of a user's body.

7. The gown dispenser system of claim 5, wherein the back region extends down to a lower extremity of the arm openings.

8. The gown dispenser system of claim 4, wherein each gown further comprises opposing left and right sleeves integral with the corresponding left and right arm openings.

9. The gown dispenser system of claim 8, wherein each gown is folded by folding the left and right sleeves against the front region, and folding a lower part of the front apron portion upward against the front region along a substantially horizontal line, leaving the back region free.

10. The gown dispenser system of claim 1, wherein each gown further comprises a pull tab attached to the back region.

11. The gown dispenser system of claim 10, wherein the front apron portion provides a pair of tie extensions positioned and configured for tying the front apron portion around a body of a user.

12. The gown dispenser system of claim 11, wherein the interface mechanism comprises one or more brackets attached to a side of the container opposite the side providing the opening, the brackets configured to enable hanging the container from a top edge of a door.

13. A gown dispenser system, comprising:
a plurality of gowns, each gown comprising:
an upper portion having a front region and an opposing back region;
opposing left and right sleeves each having an arm opening into the upper portion;
a head opening positioned in the upper portion; and
a front apron portion integral with and extending downwardly from the front region, such that the back region has a length that is shorter than the front apron portion;
the plurality of gowns folded and stacked with the back region of each gown facing up, such that, grasping and pulling on the back region of a gown on top of the stack removes that gown from the stack and exposes the back region of the next gown in the stack; and
an enclosure containing the stack of gowns with the back regions facing up, the enclosure having an opening in one surface exposing at least a portion of the back region of the gown at the top of the stack, enabling a user to grasp the exposed back region, and to pull the topmost gown from the enclosure, exposing the next gown in the stack.

14. A method for providing a gown to a user from a gown dispensing system, the method comprising the steps of:
folding a plurality of gowns into a stack of gowns, such that a back region of each gown in the stack faces up;
placing the stack of gowns into an enclosure having an opening in one surface, said opening positioned for exposing at least a portion of the back region of a topmost gown at the top of the stack; and
positioning the enclosure so as to allow a user to grasp the back region of the topmost gown and pull the topmost gown from the enclosure, leaving a next gown in the stack having the back region exposed through the opening.

15. The method of claim 14, wherein the step of folding the plurality of gowns further comprises the steps of:
folding opposing left and right sleeves of each gown against a front region of said gown, and
folding a lower part of a front apron portion of each gown upward against the front region along a substantially horizontal line, leaving the back region of said gown free.

16. The method of claim 14, wherein the step of positioning the enclosure further comprises the step of positioning the enclosure in a substantially vertical orientation, such that the back region of the topmost gown lies in a substantially vertical plane.

17. The method of claim 16, wherein the step of positioning the enclosure in a substantially vertical orientation further comprises the step of supporting the enclosure on a substantially vertical surface by an interface mechanism with the opening in the back surface facing away from the substantially vertical surface.

18. The method of claim 17, further comprising the step of positioning the enclosure on the substantially vertical surface such that a height of the opening is substantially equal to that of a height of the user.

19. The method of claim 14, further comprising the steps of:
   the user grasping and pulling the back region of the topmost gown through the opening of the enclosure;
   the user pulling an upper portion of the topmost gown over their head;
   the user inserting their head through a head opening positioned in the upper portion; and
   the user stepping back away from the enclosure, pulling a remainder of the topmost gown from the enclosure.

20. The method of claim 19, further comprising the step of the user inserting their arms into opposing left and right sleeves of the topmost gown.

\* \* \* \* \*